United States Patent [19]

Miwa et al.

[11] Patent Number: 5,268,367
[45] Date of Patent: Dec. 7, 1993

[54] COMPOSITION AND METHOD FOR LOWERING BLOOD LEVEL OF LDL-CHOLESTEROL

[75] Inventors: Toshiaki Miwa; Takayoshi Hidaka; Yoji Hisada, all of Kobe; Takehiko Ohfuji, Nara, all of Japan; Y. Pomeranz, Pullman, Wash.

[73] Assignee: Kanegafuchi Kagaku Kogyo Kabushiki Kaisha, Osaka, Japan

[21] Appl. No.: 814,642

[22] Filed: Dec. 30, 1991

[51] Int. Cl.⁵ .............. A23L 1/0522; A61K 31/715
[52] U.S. Cl. .......................................... 514/60; 514/824; 514/909; 514/911; 426/804; 426/810
[58] Field of Search .............. 514/60, 824, 909, 911; 426/804, 810

[56] References Cited

U.S. PATENT DOCUMENTS

| | | | |
|---|---|---|---|
| 4,121,974 | 10/1978 | Hofreiter et al. | 435/275 |
| 4,219,571 | 8/1980 | Miyake | 435/99 |
| 4,734,365 | 3/1988 | Haga et al. | 435/99 |
| 4,833,128 | 5/1989 | Solomon et al. | 514/909 |
| 5,023,245 | 6/1991 | Kuhrts | 514/911 |
| 5,051,271 | 9/1991 | Iyengar et al. | 426/804 |
| 5,091,524 | 2/1992 | Vértesy et al. | 514/909 |
| 5,126,332 | 6/1992 | Ohta et al. | 514/911 |
| 5,137,716 | 8/1992 | Weisenfeld | 514/911 |
| 5,145,678 | 9/1992 | Gakic et al. | 514/824 |

FOREIGN PATENT DOCUMENTS 506166  9/1992  European Pat. Off. .

OTHER PUBLICATIONS

The American Jnl. of Gastroenterology, vol. 85, No. 5, May 1990, pp. 549-553.

*Primary Examiner*—Ronald W. Griffin
*Attorney, Agent, or Firm*—Armstrong, Westerman, Hattori, McLeland & Naughton

[57] ABSTRACT

A cholesterol or body weight regulating material comprising an enzyme resistant starch is disclosed. A composition which contains said enzyme resistant starch is also disclosed. A food, food material, and beverage, containing said enzyme resistant starch are further disclosed. A method for regulating cholesterol or body weight is still further disclosed. Those are effective not only for lowering cholesterol level, but for preventing obesity.

2 Claims, No Drawings

COMPOSITION AND METHOD FOR LOWERING BLOOD LEVEL OF LDL-CHOLESTEROL

BACKGROUND OF THE INVENTION

1. Field of the Invention

The present invention relates to a cholesterol regulating material, a cholesterol or body weight regulating composition which contains an enzyme resistant starch (hereinafter referred to as "RS") as an active ingredient for regulation of cholesterol and for prevention of obesity, and to a food, food material and beverage, and method for regulating cholesterol or body weight.

2. Description of the Prior Art

Recently, attention has been paid to dietary fibers with the worldwide increasing interest in healthy diet life. Specifically, dietary fibers are being clarified to be effective for prevention of obesity and diseases of adults (such as arteriosclerosis, diabetes, cardiopathy, cancer, etc.), from the scientific and biological view. In particular, there are various reports to refer to the fact that dietary fibers are effective for inhibiting elevation of cholesterol level in blood, which is considered to be highly related to arteriosclerosis and ischemic cardiopathy. For instance, most of such dietary fibers are composed of ingredients of non-starchy vegetable polysaccharides, such as pectin (fruits), mannan (konjak or devil's-tongue), betaglucan (oats), hemicellulose, cellulose (corn, wheat, barley), etc.

Where dietary fibers are applied to those who need them for the purpose of inhibiting elevation of the cholesterol level in blood or for other various purposes, the physiological effect often varies in accordance with the kind of the dietary fibers or the effect is often sufficient only when a fairly large amount of dietary fibers are taken. However, in the case of foods from which a large amount of dietary fibers are to be taken, the quality of such foods is often lowered as the foods of themselves in view of the taste or texture thereof and such foods would not meet with consumer acceptance. As a result, such foods could not be said to be always suitable for continuous ingestion.

As an example of non-starchy vegetable polysaccharide is known CELLACE (registered trade mark by Nippon Food Processing Co.) which comprises arabinoxylan as an active ingredient. However, this is not sufficiently satisfactory, like other dietary fibers, in the point of preventing elevation of cholesterol level in blood, especially low-density-lipoprotein-cholesterol (hereinafter referred to as "LDL-cholesterol") therein which is said to be positively related to arteriosclerosis.

With respect to the point of the effect of lowering the LDL-cholesterol in blood, cholestyramine (for example, QUESTRAN: registered trade mark by Bristol-Myers Co.) is excellent, which is a chemical synthetic product. The cholestyramine of a medicine for hyperlipidemia is an anion-exchange resin as the element in itself and it is known that the cholestyramine acts to absorb bile acid in intestines and, as a result, lowers the cholesterol level in blood. However, it has an objectionable taste because of the characteristic of the resin of itself, and sweeteners or the like are added thereto for the purpose of reducing the unfavorable taste as much as possible. Despite of such addition, there still remains the problem that the cholestyramine could not be administered with ease. Accordingly, some other substitutes for it, which may easily be administered, are desired.

SUMMARY OF THE INVENTION

An object of the present invention is to find out a material which has an effect of preventing an elevation of cholesterol level in blood or of lowering the same in blood, not from chemical synthetic products but from edible grains, vegetables, fruits or cooked or processed products thereof, and to provide foods, food materials, beverages or medical compositions containing the found component.

Another object of the present invention is to provide a composition containing the material, which is effective for lowering cholesterol or body weight.

Still another object of the present invention is to provide a food, food material or beverage containing the material.

A further object of the present invention is to provide a method for lowering cholesterol or body weight, or for preventing an elevation of cholesterol or body weight.

Other objects and the advantages of the present invention will become apparent from the detailed disclosure as described below.

The present inventors conducted intensive studies to attain the above objective and, as a result, have found that a so-called RS which is produced from an alpha-amylas-treated residue of retrograded starch as obtained by cooling a gelatinized starch, has an effect of lowering cholesterol level in blood and an effect of preventing obesity. Accordingly, on the basis of the finding, we have completed the present invention.

DETAILED DESCRIPTION OF THE INVENTION

The present invention relates, in a first aspect, to an enzyme resistant starch which is useful for lowering and/or preventing an elevation of a cholesterol level in blood.

The present invention is, in a second aspect, to provide a composition for lowering a cholesterol level in blood, which contains an effective amount of an enzyme resistant starch.

The present invention is, in a third aspect, to provide a composition for preventing an elevation of a cholesterol level in blood when a high cholesterol content diet is taken, which contains an effective amount of an enzyme resistant starch.

The present invention is, in a fourth aspect, to provide a composition for regulating body weight which contains an effective amount of an enzyme resistant starch.

The present invention is, in a fifth aspect, to provide a composition for preventing an elevation of body weight when a high cholesterol content diet is taken, which contains an effective amount of an enzyme resistant starch.

The present invention is, in a sixth aspect, to provide a high cholesterol content food which contains an effective amount of an enzyme resistant starch.

The present invention is, in a seventh aspect, to provide a high cholesterol content food material which contains an effective amount of an enzyme resistant starch.

The present invention is, in an eight aspect, to provide a method for preventing an elevation of a cholesterol level which comprises taking a high cholesterol content diet and an effective amount of an enzyme resistant starch.

The present invention is, in a ninth aspect, to provide a method for preventing an elevation of body weight which comprises taking a high cholesterol content diet and an effective amount of an enzyme resistant starch.

The present invention is, in a tenth aspect, to provide a method for lowering an excessive level of cholesterol which comprises taking an effective amount of an enzyme resistant starch.

The present invention is, in an eleventh aspect, to provide a method for regulating body weight which comprises taking an effective amount of an enzyme resistant starch.

RS is a general name of a substance which is obtained by gelatinizing raw starch in an autoclave, cooling it to give retrograded starch, alpha-amylase-treating retrograded starch and thereafter purifying the starch [D. Sievert and Y. Pomeranz; Enzyme-resistant starch, I. Cereal Chem. 66, 342–347 (1989); II. Cereal Chem. 67, 217–221 (1990); Y. Pomeranz and D. Sievert; Purfied resistant starch products and their preparation; U.S. patent application Ser. No. 363,253].

It comprises an amylose-like molecule and is characterized in that, when it is solubilized with an alkali (for example, in KOH solution) or with dimethyl-sulfoxide, it is degraded by alpha-amylase to liberate glucose [M. Silzestrom; Starch/Stark, 41, 147 (1989)].

Where it is actually used, it need not be in the form of a pure RS and it can contain any other substances which are harmless to human bodies when they are taken, for example, in the form of a starch fraction consisting of RS mainly.

The method of preparing RS is basically mentioned above. Additionally, some modified methods are known.

For instance, one modified method is illustrated herein as the following Production Example. Additionally, RS may also be prepared by the methods described in J. Cereal Science, 6, 159 (1987); J. Sci. Food Agric., 44, 281 (1981); Brit. J. Nutrition, 61, 291 (1989).

As a starch to be usable as a starting material for forming RS, there are mentioned, for example, raw starch of corn, potato, bean, wheat or rice, as well as soluble starch, or amylose of itself, or high amylose-starch (e.g., amylomaise, etc.), or dextrin obtained by cleavage of the 1,6-bond of amylopectin.

There are several reports as to whether RS lowers the cholesterol level in blood. For instance, it is reported by J. M. Gee et al. that when a semisynthetic diet mixed with RS, to which cholesterol was not added, in particular, was administered to rats, increases in fecal bulk, cecal size and content were observed, but the cholesterol level in blood was not affected [J. Nutrition; 121, 44 (1991)]. You need a reference to de Decker et al. that when a purified diet mixed with 20% by weight of RS, to which cholesterol was not added, was administrated to rats, the cecal content was increased as compared with a case where a purified diet mixed with 1% by weight of RS was administered, but the cholesterol level in blood was not varied. Both reports conclude that an effect of lowering the cholesterol level in blood was not admitted upon investigation into an effect of RS on the cholesterol level in blood under conditions in which cholesterol was not specifically added.

Where such RS is taken along with a high cholesterol diet, the total cholesterol and LDL-cholesterol in blood are decreased.

Since the amount of the LDL-cholesterol in blood which has a high relation to arteriosclerosis is reduced, the effect of inhibiting arteriosclerosis can be expected. Further, since the increase of the body weight to be caused by ingestion of a high cholesterol diet can be prevented by administration of RS of the kind and the body weight can be maintained to be the same level as that to be attained by ingestion of a normal diet, RS also has an effect of preventing obesity.

The high choresterol diet comprises foods, food materials and/or beverages, which provide a person per one day with more than 300 mg cholesterol, the level of which is above a guideline figure for human health.

For actually taking or ingesting RS, there are various methods. For instance, RS may directly be eaten as a powder thereof, or as an edible composition comprising RS and water, RS and food materials, RS and foods, RS and beverages or RS and seasonings. That is to say, RS is incorporated into fat and oil products such as margarine or shortening, into egg products such as egg yolk or mayonnaise, into dairy products such as milk, yogurt or cheese, into cereal products such as corn or wheat flour, into fruit juice, or into other foods or food materials; or RS is processed into beverages or foods of bread, cake, biscuit, cereal, noodle or juice; or RS of itself is seasoned to give a seasoned RS food. In the edible composition, high cholesterol foods, high cholesterol food materials or high cholesterol beverages can be used as components of the composition. In addition, RS is blended with a carrier to give a medical composition. The thus prepared RS-containing foods, beverages, food materials or medical preparations may be ingested. As medical preparations, any orally administratable ones may be employed, which include tablets, capsules, granules, fine grains, syrup or suspension.

The amount of RS to be taken or ingested varies depending upon the amount of cholesterol as ingested or upon the amount (concentration) of cholesterol in blood, but it is preferably from 0.5 g to 150 g/adult/day or from one to 300 times (by weight) of a day's amount of cholesterol to be ingested.

It is known that RS is starch to be derived from natural substances and is formed after cooked (or retorted or baked) foods are cooled. For instance, in some cases, heat processed products of bread, beans or potatos may contain RS in an amount of 3% by weight maximum. Accordingly, RS is a food material which has heretofore been taken by human beings for a long period of time and is therefore considered to pose no problem in oral administration.

Next, Production Example of producing RS, Test Examples of testing it, and Formulation Example of containing it are mentioned below.

In the following description, "parts" and "%" mean "parts by weight" and "% by weight", respectively, unless otherwise indicated.

PRODUCTION EXAMPLE 4 parts of water was added to 200 g of amylomaize starch (amylose content: 70%) and heated in an autoclave at 121° C. for one hour. After cooled, the gelatinized starch was mechanically ground and then incubated at 100° C. for one hour along with Termamyl (bacteria-derived heat stable alpha-amylase). After the enzymatic treatment, the starch was heated in an autoclave at 134° C. for 5 minutes for deactivating the Termamyl and thereafter washed with a sufficient amount of water and then with ethanol five to six times. This was then dried in vacuum and ground to 32 g of a powder. The RS content in the powder was measured in accordance with the AOAC method of measuring dietary fibers (J. Assoc. off. Aml. Chem., 68, 399, 1985) to be 71%.

TEST EXAMPLE 1

Syrian male hamsters (4-week age) were used, and these were pre-fed on a commercially available solid feed for 8 days. The pre-fed hamsters with no abnormality were selected and subjected to a test in one group having 5 hamsters. During the durations of pre-feeding and test-feeding, the feed and water were given freely.

To hamsters belonging to control groups, were administered high cholesterol content diets obtained by adding 1.5% of cholesterol, 0.5% of cholic acid and 5% of olive oil to a commercially available diet and to hamsters belonging to RS, arabinoxylan and cholestyramine groups, were administered diets obtained by adding further 2% of RS prepared by the foregoing Production Example, and 4% of arabinoxylan or 2% of cholestyramine, respectively, to said high cholesterol content diets.

As the arabinoxylan, CELLACE (registered trade mark by Nippon Food Processing Co.) was used and as the cholestyramine, QUESTRAN (registered trade mark by Bristol-Myers Co.), a medicine for hyperlipidermia was used in terms of 2% of cholestyramine. These diets were given freely for 4 weeks and after one night fast, bloods were taken out for the measurement of serum lipid using a kit commercially available. Moreover, the relationship between an increase in body weight and an intake of diet was investigated. The significant difference test was made by Student's t-test.

As shown by Table 1, RS lowered the total cholesterol and LDL-cholesterol in the serum of hamsters by 25% and 32%, respectively, but hardly influenced HDL-cholesterol. On the other hand, neither arabinoxylan nor cholestyramine for comparison exhibited an effect of lowering the total cholesterol.

Moreover, as shown by Table 2, RS exhibited an effect of preventing obesity from nutritional efficiency obtained from an increase in body weight per intake of diet.

TEST EXAMPLE 2

The test was carried out on Syrian male hamsters (4-week age) in the same manner as in Test Example 1, except for some modifications.

That is, to hamsters belonging to control groups were administered high cholesterol content diets obtained by adding 0.75% of cholesterol, 0.25% of cholic acid and 5% of olive oil to a commercially available diet and to hamsters belonging to RS, arabinoxylan, oatfiber or cholestyramine were administered diets obtained by adding further 2% of RS prepared by the foregoing Production Example, 4% of arabinoxylan, 4% of oatfiber or 2% of cholestyramine, respectively, to said high cholesterol content diets. Arabinoxylan and cholestyramine were the same as used in Test Example 1 and oatfiber BETTER BASICS 780 (resistered trade mark by Williamson Fiber Products, Inc.) was employed.

As apparent from Table 3, RS lowered the total cholesterol and LDL-choresterol in the serum of hamsters by 12% and 17%, respectively, but had no influence on HDL-cholesterol.

In contrast, among the control examples for comparison, cholestyramine lowered the total cholesterol and LDL-cholesterol by 18% and 19%, respectively, while two kinds of dietary fibers, arabinoxylan and oatfiber, provided no effect of lowering the total cholesterol.

Moreover, as shown by Table 4, RS was found to have an effect of preventing obesity from nutritional efficiency which was calculated from the increased body weight and the intake of diet.

It is known that when hamsters are fed on normal diets, the values of the total cholesterol, HDL-cholesterol and LDL-cholesterol are comparatively analogous to those of human beings. The results obtained by the test performed in parallel were 209, 81 and 128 mg/dl, respectively.

Accordingly, it is understood that when high cholesterol content diets are given to the hamsters having such a serum lipid pattern, RS provides a significant effect of suppressing an increase in LDL-cholesterol level as compared with control examples.

In addition, RS shows less increase in body weight with respect to the intake of diet, exhibiting a suppressing effect of obesity from the viewpoint of nutritional effeciency of diets.

TEST EXAMPLE 3

A noodle was prepared by mixing with wheat flour, RS, and wheat bran and soy bean fiber for comparison, in an amount of 4%, respectively. The obtained noodle was evaluated in color before and after cooking, texture after cooking and yield and compared with a control noodle not containing dietary fibers. Scores were given to each characteristic of the control noodle, 16, 16, 32, 16, respectively, and 80 in total, and 16 or 32 was given when each characteristic was the same level as that of the control noodle or higher, while lower scores were given when lower than that of the control noodle.

Table 5 reveals that the noodle containing RS is higher in the total score than any other noodle containing other additives, and especially superior in color.

| Formulation Example | |
|---|---|
| RS | 80 g |
| Corn Starch | 4 |
| Lactose | 10 |
| Calcium Carboxymethyl Cellulose | 4 |
| Methyl Cellulose | 1.5 |
| Magnesium Stearate | 0.5 |
| Total | 100 g |

In accordance with the above-mentioned formulation, all the components were uniformly blended and shaped into tablets by compression shaping with a tableting machine.

As explained in detail in the above, RS has a positive effect of obviously lowering cholesterol level in blood. Accordingly, a medical composition containing it can be used as a preventive or remedial medicine for hyperlipidemia, arteriosclerosis, etc.

Further, as RS has an additional effect of preventing obesity and it can well be incorporated into various foods without interfering with the intrinsic color, taste and texture of the foods themselves, it can continuously be ingested along with foods, the food containing RS are excellent healthy foods or can be part of a cholesterol-containing diet capable of preventing and curing hyperlipidemia in view of the points that RS is effective for not increasing cholesterol level in blood, especially LDL-cholesterol therein, and that it is also effective for preventing obesity.

TABLE 1

Effect on serum lipid

| | T-C | HDL-C | LDL-C | TG (mg/dl) | PL |
|---|---|---|---|---|---|
| Control (No addition of dietary fiber) | 435 ± 62 | 123 ± 7 | 312 ± 68 | 254 ± 72 | 380 ± 22 |
| RS 2% | 325 ± 65* | 114 ± 11 | 211 ± 59* | 252 ± 40 | 317 ± 48* |
| Arabinoxylan 4% | 411 ± 40 | 137 ± 6* | 274 ± 40 | 319 ± 72 | 383 ± 16 |
| Cholestyramine 2% | 546 ± 93 | 118 ± 30 | 427 ± 119 | 417 ± 241 | 464 ± 125 |

T-C: Total cholesterol TG: neutral fat PL: phospholipid
*: $P < 0.05$

TABLE 2

Effect on body weight and intake of diet (Duration: 4 weeks)

| | Increase in body weight (g) | Intake of diet (g) | Nutritional efficiency (Increase in body weight/Intake of diet) |
|---|---|---|---|
| Control (No addition of dietary fiber) | 25 ± 5 | 175 | 0.141 |
| RS 2% | 17 ± 8 | 156 | 0.111 |
| Arabinoxylan 4% | 21 ± 4 | 163 | 0.127 |
| Cholestyramine 2% | 34 ± 4 | 191 | 0.178 |

TABLE 3

Effect on serum lipid

| | T-C | HDL-C | LDL-C | TG (mg/dl) | PL |
|---|---|---|---|---|---|
| Control (No addition of dietary fiber) | 378 ± 28 | 133 ± 11 | 245 ± 35 | 233 ± 23 | 371 ± 21 |
| RS 2% | 333 ± 28* | 130 ± 13 | 203 ± 19* | 205 ± 26 | 338 ± 26# |
| Arabinoxylan 4% | 375 ± 39 | 127 ± 10 | 248 ± 31 | 257 ± 81 | 359 ± 37 |
| Oatfiber 4% | 390 ± 20 | 131 ± 7 | 259 ± 21 | 201 ± 36 | 358 ± 14 |
| Cholestyramine 2% | 312 ± 36* | 113 ± 10* | 199 ± 44 | 264 ± 27* | 320 ± 12** |

T-C: Total cholesterol TG: neutral fat PL: phospholipid
: $P < 0.1$  *: $P < 0.05$  **: $P < 0.01$

TABLE 4

Effect on body weight and intake of diet (Duration: 4 weeks)

| | Increase in body weight (g) | Intake of diet (g) | Nutritional efficiency (Increase in body weight/Intake of diet) |
|---|---|---|---|
| Control (No addition of dietary fiber) | 29 ± 7 | 174 | 0.167 |
| RS 2% | 21 ± 6 | 160 | 0.130 |
| Arabinoxylan 4% | 23 ± 2 | 159 | 0.147 |
| Oatfiber 4% | 26 ± 8 | 176 | 0.147 |
| Cholestyramine 2% | 28 ± 5 | 174 | 0.163 |

TABLE 5

Evaluation of noodle

| | Color (Before cooking) | Color (After cooking) | Texture (After cooking) | Yield | Total |
|---|---|---|---|---|---|
| Control (No addition of dietary fiber) | 16 | 16 | 32 | 16 | 80 |
| RS | 16 | 16 | 28 | 15 | 75 |
| Wheat bran | 11 | 12 | 30 | 16 | 69 |
| Soy bean fiber | 12 | 14 | 30 | 16 | 72 |

What is claimed is:

1. A method for preventing the elevation of the LDL-cholesterol level in the blood of an animal, which comprises administering an effective amount of an enzyme resistant starch to the animal in combination with a high cholesterol diet.

2. A method for lowering the LDL-cholesterol level in the blood of an animal, which comprises administering an effective amount of an enzyme resistant starch to the animal in combination with a high cholesterol diet.

* * * * *